United States Patent [19]

Ghosh

[11] Patent Number: 5,725,806
[45] Date of Patent: Mar. 10, 1998

[54] DISULFIDE STABILIZERS FOR 3-ISOTHIAZOLONES

[75] Inventor: Tirthankar Ghosh, Oreland, Pa.

[73] Assignee: Rohm and Haas Company, Philadelphia, Pa.

[21] Appl. No.: 747,102

[22] Filed: Nov. 8, 1996

Related U.S. Application Data

[60] Provisional application No. 60/008,206 Dec. 5, 1995.
[51] Int. Cl.⁶ .................................................. C07D 277/14
[52] U.S. Cl. ..................... 252/405; 548/213; 548/158; 548/252; 546/261
[58] Field of Search ................................ 548/213, 158, 548/252; 546/261; 252/405

[56] References Cited

U.S. PATENT DOCUMENTS 5,210,094  5/1993  Reeve .................................. 514/372

FOREIGN PATENT DOCUMENTS 2208474  4/1989  United Kingdom.

Primary Examiner—Johann Richter
Assistant Examiner—Laura Cross Lutz
Attorney, Agent, or Firm—Julie J. L. Cheng

[57] ABSTRACT

A method of stabilizing non-halogen containing 3-isothiazolone microbicides against chemical degradation by the introduction of aromatic disulfide compounds (except 2,2'-dithiobisbenzoic acid) is disclosed.

8 Claims, No Drawings

DISULFIDE STABILIZERS FOR 3-ISOTHIAZOLONES

This is a nonprovisional application of prior pending provisional application serial no. 60/008,206, filed Dec. 5, 1995.

This invention relates to the stabilization of 3-isothiazolone microbicides and their use in controlling microorganisms.

3-Isothiazolones are a class of commercially important microbicides. They are useful in both aqueous and non-aqueous products to prevent spoilage caused by microorganisms. Because of their versatility, 3-isothiazolones have found use in a variety of applications. Commercially important 3-isothiazolones include 5-chloro-2-methyl-3-isothiazolone (or 5-chloro-2-methyl-4-isothiazolin-3-one), 2-methyl-3-isothiazolone (or 2-methyl-4-isothiazolin-3-one), 2-n-octyl-3-isothiazolone (or 2-n-octyl-4-isothiazolin-3-one), and 4,5-dichloro-2-n-octyl-3-isothiazolone (or 4,5-dichloro-2-n-octyl-4-isothiazolone-3-one).

It has long been recognized that 3-isothiazolones are generally not stable under practical conditions of long term storage. 3-Isothiazolones may degrade in storage either prior to or after addition to a system to be protected. Also, 3-isothiazolones are used in a number of applications that contain agents that are aggressive toward 3-isothiazolones, e.g. metal working fluids. Such aggressive agents decrease the efficacy of the 3-isothiazolone. Means have thus been sought for some time to improve the stability of 3-isothiazolones.

Certain organic stabilizers have been found for 3-isothiazolones. These are an improvement over the older inorganic stabilizers in a number of applications. U.S. Pat. No. 5,210,094 discloses a class of sulfur containing organic compounds as stabilizers for 3-isothiazolones which are particularly useful in metal working fluid concentrates. These stabilizers lock up the 3-isothiazolones in the form of adducts, which are resistant to chemical degradation. Such adducts release the 3-isothiazolone when needed simply upon dilution of the product.

A problem with these stabilizers is that they require adduct formation to stabilize the 3-isothiazolones. Once these stabilized 3-isothiazolone concentratess are diluted, as is the case when 3-isothiazolone containing metal working fluid concentrates are added to a metal working fluid, the adducts fall apart and the released 3-isothiazolone is no longer stablized. In metal working fluid systems with aggressive agents, this poses a significant problem.

I have discovered a class of stabilizing compounds for non-halogen containing 3-isothiazolones which does not form an adduct with the 3-isothiazolones. These stabilizers are useful in both concentrated and diluted forms of the 3-isothiazolones. These stabilizers also protect the non-halogen containing 3-isothiazolones against attack by aggressive agents, such as those found in metal working fluids.

By concentrated forms of 3-isothiazolones are meant the solid 3-isothiazolone itself and from 5 to 50% of the 3-isothiazolones in water or an organic solvent. By diluted forms of 3-isothiazolones are meant from 1 to 5% of 3-isothiazolones in water or an organic solvent and from 0.001 to 1% of 3-isothiazolones in water, an organic solvent, or a locus to be protected.

An aspect of the invention comprises a method of stabilizing non-halogen containing 3-isothiazolone microbicides comprising introducing to said 3-isothiazolone at least one aromatic disulfide compound in an amount sufficient to stabilize said 3-isothiazolone, provided said aromatic disulfide compound is not 2,2'-dithiobisbenzoic acid.

Another aspect of the invention comprises a composition comprising 3-isothiazolone microbicides and at least one aromatic disulfide compound in an amount sufficient to stabilize said 3-isothiazolone, provided said aromatic disulfide compound is not 2,2'-dithiobisbenzoic acid.

The preferred 3-isothiazolones are 2-methyl-3-isothiazolone ("MI"); 2-n-octyl-3-isothiazolone ("OI"); 2-ethyl-3-isothiazolone; and mixtures thereof.

The aromatic disulfide compounds useful as stabilizers in this invention are those derived from relatively non-nucleophilic aromatic thiols. Suitable aromatic disulfide stabilizers include 2,2'-dithiobis(pyridine-N-oxide) ("DTPNO"); 5,5'-dithiobis(2-nitrobenzoic acid) ("DTNB"); 2,2'-dithiobis(pyridine); 2,2'-dithiobis(benzothiazole); 2,2'-dithiobis(5-nitropyridine); and 5,5'-dithiobis(1-phenyl-1-H-tetrazole).

The ratio of non-halogen containing 3-isothiazolone to aromatic disulfide compound is from 10:1 to 1:10. The preferred ratio is from 5:1 to 1:5. The most preferred ratio is from 2:1 to 1:2.

The compositions of the invention may additionally contain solvent. Suitable solvents are any which dissolve the 3-isothiazolone and the disulfide stabilizer, are compatible with the end use of the composition, do not destabilize the isothiazolone and do not react with the disulfide stabilizer to prevent its stabilizing action.

Suitable solvents include, for example, polyols, such as glycols and alcohol; capped polyols, aromatic hydrocarbons; aliphatic hydrocarbons; and water.

The compositions of the invention are prepared by combining non-halogen containing 3-isothiazolone, aromatic disulfide stabilizer, and optional solvent in any order.

The amount of non-halogen containing 3-isothiazolone added to a locus to control the growth of microorganisms depends upon the particular 3-isothiazolone and the locus to be protected. Typical amounts are 3–2000 ppm of 3-isothiazolone based upon the locus.

It is known in the art that the performance of microbicides may be enhanced by combination with one or more other microbicides. Thus, other known microbicides may be combined advantageously with the compositions of this invention.

The stabilized compositions of this invention may be used in any locus subject to contamination by bacteria, fungi, or algae. Typical loci are in systems such as cosmetics; household products; fuel; mineral slurries; metal working fluids; latices; paints; coatings, such as caulks, mastics, and varnishes; and cooling towers. The composition is especially useful to protect metal working fluids.

All reagents were good commercial grade and used without further purification. Analyses for 3-isothiazolones were performed by reverse phase HPLC with UV detection.

EXAMPLE 1

This example demonstrates the stabilizing effect of the disulfides on MI in a model metal working fluid.

A model metal working fluid was prepared by combining distilled water (42.3%), propylene glycol (42.3%), monoethanolamine (10%), diethanolamine (0.2%), boric acid (5%), and 50% sodium hydroxide (0.3%). The fluid had a pH of 9.7. Equal portions of this fluid were added to each of three screw cap, glass vials. To each vial were added 1000 ppm MI. To a first vial were added 1000 ppm of DTPNO as stabilizer. To a second vial were added 1000 ppm of DTNB as stabilizer. No stabilizer was added to the third vial. The third vial served as a control. The samples were capped and stored in an oven at 40° C. Aliquots were removed after 1, 2, and 4 weeks and were analyzed for MI remaining. The results are shown in Table 1.

TABLE 1

| Sample | Stabilizer | % MI Remaining | | |
|---|---|---|---|---|
| | | 1 Week | 2 Weeks | 4 Weeks |
| 1 | DTPNO | 100 | 100 | 100 |
| 2 | DTNB | 98 | 91 | 87 |
| 3 | None | — | 0 | NA |

NA = not analyzed

From these data it can be seen that both DTPNO and DTNB are effective stabilizers for 3-isothiazolones.

EXAMPLE 2

This example demonstrates the stabilizing effect of the disulfides on MI in an industrial metal working fluid.

To each of four samples containing a commercial water based, amine containing semi-synthetic metal working fluid having a pH of 9.2 were added 2000 ppm of MI. To two of the samples were added 1000 ppm of DTPNO as stabilizer. The remaining two samples served as controls. One control and one stabilized sample were stored at 25° C. The remaining control and stabilized sample were stored at 35° C. The samples were analyzed after eight weeks storage. The results are reported in Table 2.

TABLE 2

| | % MI Remaining after 8 Weeks Storage | |
|---|---|---|
| Samples | 25° C. | 35° C. |
| Control | 49.7 | 9.6 |
| Stabilized sample | 91.3 | 81.5 |

From these data it can be seen that the aromatic disulfide stabilizer greatly enhances the stability of the 3-isothiazolones compared to no stabilizer.

EXAMPLE 3

This example compares the stabilizing effect of aromatic disulfides with the corresponding prior art aromatic mercaptan stabilizer on OI in an industrial metal working fluid. The sodium salt of 2-mercaptopyridine N-oxide ("NaPNO") is disclosed as a stabilizer for 3-isothiazolones in U.S. Pat. No. 5,210,094.

Five samples of a commercial water based, boron- and amine-containing semi-synthetic metal working fluid were prepared. To each sample were added approximately 1000 ppm of OI. No stabilizer was added to the first sample, which served as a control. To the second sample was added approximately 1000 ppm of NaPNO. To the remaining three samples were added 1000, 500, and 250 ppm of DTPNO respectively, as stabilizer. Each of the five samples was split in half. One half of each sample was stored at 25° C. and the other half at 35° C. The samples were analyzed at various time points. The results are reported in Table 3.

TABLE 3

| Sample | OI (ppm) | Stabilizer (ppm) | OI: Stabilizer | % OI Remaining | | |
|---|---|---|---|---|---|---|
| | | | | 25° C. 1 Wk | 35° C. 1 Wk | 2 Wks |
| 1* | 848 | None | | 0 | 0 | — |
| 2* | 967 | NaPNO (903) | | 98 | 97 | 92 |
| 3 | 874 | DTPNO (971) | 1:1.1 | 95 | 94 | 92 |
| 4 | 992 | DTPNO (493) | 2:1 | 98 | 96 | 93 |
| 5 | 924 | DTPNO (234) | 4:1 | 97 | 94 | NA |

*= comparative
NA = not analyzed

These data show that 250 ppm of the aromatic disulfide stabilizers of the invention are as effective in stabilizing 3-isothiazolones against chemical degradation as are 900 ppm of the prior art aromatic mercaptan stabilizers.

EXAMPLE 4

This example compares the stabilizing effect of aromatic disulfides with the corresponding prior art aromatic mercaptan stabilizer, NaPNO, on MI in an industrial metal working fluid.

The procedure of Example 3 was followed except that approximately 2500 ppm of MI was used insted of OI, and the samples were stored at only 25∞ C. The results are reported in Table 4.

TABLE 4

| Sample | MI (ppm) | Stabilizer (ppm) | MI:Stabilizer | % MI Remaining 25° C. | |
|---|---|---|---|---|---|
| | | | | 1 Wk | 2 Wks |
| 1* | 2496 | None | | 0 | — |
| 2* | 2559 | NaPNO (993) | | 76 | 0 |
| 3 | 2555 | DTPNO (978) | 2.6:1 | 97 | 95 |
| 4 | 2606 | DTPNO (495) | 5.3:1 | 96 | 84 |
| 5 | 2423 | DTPNO (241) | 10:1 | 92 | 0 |

*= comparative
NA = not analyzed

From these data it can be seen that the aromatic disulfide stabilizers of the invention are more effective at stabilizing MI than the prior art aromatic mercaptan stabilizers.

What is claimed is:

1. A method of stabilizing non-halogen containing 3-isothiazolone microbicides comprising introducing to said 3-isothiazolone at least one aromatic disulfide compound in an amount sufficient to stabilize said 3-isothiazolone, provided said aromatic disulfide compound is not 2,2'-dithiobisbenzoic acid.

2. Method according to claim 1 wherein said aromatic disulfide compound is selected from the group consisting of 2,2'-dithiobis(pyridine-N-oxide); 5,5'-dithiobis(2-nitrobenzoic acid); 2,2'-dithiobis(pyridine); 2,2'-dithiobis (benzothiazole); 2,2'-dithiobis(5-nitropyridine); and 5,5'-dithiobis(1-phenyl-1-H-tetrazole).

3. Method according to claim 1 wherein said 3-isothiazolone is selected from the group consisting of 2-methyl-3-isothiazolone; 2-n-octyl-3-isothiazolone; 2-ethyl-3-isothiazolone; and mixtures thereof.

4. Method according to claim 1 wherein the ratio of said 3-isothiazolone to said aromatic disulfide compound is from 10:1 to 1:10.

5. A composition comprising 3-isothiazolone microbicides and at least one aromatic disulfide compound selected from the group consisting of 2,2'-dithiobis(pyridine-N-oxide); 5,5'-dithiobis(2-nitrobenzoic acid); 2,2'-dithiobis(pyridine); 2,2'-dithiobis(benzothiazole); 2,2'-dithiobis(5-nitropyridine); and 5,5'-dithiobis(1-phenyl-1-H-tetrazole), wherein the aromatic disulfide is present in an amount sufficient to stabilize said 3-isothiazolone.

6. Composition according to claim 5 wherein said 3-isothiazolone is selected from the group consisting of 2-methyl-3-isothiazolone; 2-n-octyl-3-isothiazolone; 2-ethyl-3-isothiazolone; and mixtures thereof.

7. Composition according to claim 5 wherein the ratio of said 3-isothiazolone to said aromatic disulfide compound is from 10:1 to 1:10.

8. Composition according to claim 5 where in said 3-isothiazolone is selected from the group consisting of 2-methyl-3-isothiazolone and 2-n-octyl-3-isothiazolone; said aromatic disulfide compound is selected from the group consisting of 2,2'-dithiobis(pyridine-N-oxide) and 5,5'-dithiobis(2-nitrobenzoic acid); and the ratio of said 3-isothiazolone to said aromatic disulfide compound is from 1:10 to 10:1.

* * * * *